US012797382B2

(12) United States Patent
Kim

(10) Patent No.: US 12,797,382 B2
(45) Date of Patent: *Nov. 17, 2026

(54) SUSTAINED-RELEASE INJECTABLE COMPOSITION CONTAINING NALTREXONE AND METHOD FOR PREPARING SAME

(71) Applicant: INVENTAGE LAB INC., Seongnam-si (KR)

(72) Inventor: Ju Hee Kim, Seongnam-si (KR)

(73) Assignee: INVENTAGE LAB INC., Seongnam-si (KR)

( * ) Notice: Subject to any disclaimer, the term of this patent is extended or adjusted under 35 U.S.C. 154(b) by 426 days.

This patent is subject to a terminal disclaimer.

(21) Appl. No.: 18/285,002

(22) PCT Filed: Nov. 18, 2022

(86) PCT No.: PCT/KR2022/018258

§ 371 (c)(1),
(2) Date: Sep. 29, 2023

(87) PCT Pub. No.: WO2023/090922

PCT Pub. Date: May 25, 2023

(65) Prior Publication Data

US 2024/0197717 A1 Jun. 20, 2024

(30) Foreign Application Priority Data

Nov. 18, 2021 (KR) ........................ 10-2021-0159539
Nov. 17, 2022 (KR) ........................ 10-2022-0154632

(51) Int. Cl.

*A61K 31/485* (2006.01)
*A61K 9/00* (2006.01)
*A61K 9/19* (2006.01)
*A61K 9/50* (2006.01)

(52) U.S. Cl.

CPC .......... *A61K 31/485* (2013.01); *A61K 9/0019* (2013.01); *A61K 9/19* (2013.01); *A61K 9/5031* (2013.01)

(58) Field of Classification Search

None
See application file for complete search history.

(56) References Cited

U.S. PATENT DOCUMENTS

| | | | | |
|---|---|---|---|---|
| 6,306,425 | B1 | 10/2001 | Tice et al. | |
| 11,730,731 | B2 * | 8/2023 | Kim | A61K 31/485 514/282 |
| 2011/0206773 | A1 | 8/2011 | Lavik et al. | |
| 2020/0113835 | A1 * | 4/2020 | Yoon | A61K 9/1664 |
| 2020/0261878 | A1 | 8/2020 | Kim | |
| 2022/0133632 | A1 * | 5/2022 | Enomura | C08J 3/122 424/489 |
| 2022/0202894 | A1 | 6/2022 | Kim et al. | |

FOREIGN PATENT DOCUMENTS

| | | | | |
|---|---|---|---|---|
| AU | 2019401868 | A1 | 7/2021 | |
| CN | 10-7929264 | A | 4/2018 | |
| CN | 108703960 | A | 10/2018 | |
| CN | 111617043 | A | 9/2020 | |
| EP | 2327397 | A2 | 6/2011 | |
| JP | 2002-541202 | A | 12/2002 | |
| KR | 10-2002-0011975 | A | 2/2002 | |
| KR | 20100026384 | A | 3/2010 | |
| KR | 20180018985 | A1 | 2/2018 | |
| KR | 10-2018-0129909 | A1 | 12/2018 | |
| KR | 20190004189 | A1 | 1/2019 | |
| KR | 101962189 | B1 | 3/2019 | |
| KR | 20190064509 | A | 6/2019 | |
| KR | 10-2020-0044977 | A | 4/2020 | |
| KR | 20200044977 | A | 4/2020 | |
| KR | 10-2021-0065190 | A | 6/2021 | |
| KR | 10-2021-0110825 | A | 9/2021 | |
| WO | 2005-009356 | A2 | 2/2005 | |
| WO | 2017/186077 | A1 | 11/2017 | |
| WO | 2018-038461 | A1 | 3/2018 | |
| WO | 2018088731 | A1 | 5/2018 | |
| WO | 2020/080806 | A1 | 4/2020 | |
| WO | WO-2020183718 | A1 * | 9/2020 | A61K 9/1694 |
| WO | 2020/222399 | A1 | 11/2020 | |
| WO | 2021-010719 | A1 | 1/2021 | |

(Continued)

OTHER PUBLICATIONS

Hua, Y. et al., Key Factor Study for Generic Long-Acting PLGA Microspheres Based on a Reverse Engineering of Vivitrol®, Molecules, 26 (2021) pp. 1-18. (Year: 2021).*

Emmamuel O Akala et al., "Studies on in 1-10 vitro availability, degradation, and thermal properties of naltrexone-loaded biodegradable microspheres", Journal Drug Development and Industrial Pharmacy, vol. 37, No. 6, Jun. 30, 2011, pp. 673-684, XP055714626, US ISSN: 0363-9045, DOI: 10.3109/03639045.2010.535540, United States.

S. Von Eggelkraut-G, "European Search Report for EP Application No. 22896119.9", Jul. 30, 2025, EPO, Germany.

(Continued)

*Primary Examiner* — Dominic Lazaro

(74) *Attorney, Agent, or Firm* — Bridgeway IP Law Group, PLLC; Jihun Kim

(57) ABSTRACT

A sustained-release injectable composition containing naltrexone, and a method for producing the same are described. The composition may prevent the initial burst release of naltrexone by controlling the release rate of naltrexone at a target site, and maintain a plasma naltrexone concentration sufficient to exhibit the effect of naltrexone by releasing naltrexone continuously for one month. In addition, the production method is capable of producing microparticles that are homogeneous and of good quality while having high encapsulation efficiency for naltrexone, a poorly soluble drug.

9 Claims, No Drawings

(56) References Cited

FOREIGN PATENT DOCUMENTS

| | | | |
|---|---|---|---|
| WO | 2021083989 | A1 | 5/2021 |
| WO | 2021162532 | A2 | 8/2021 |
| WO | 2021162532 | A3 | 9/2021 |

OTHER PUBLICATIONS

Stefan Hartinger, "European Search Report for EP Application No. 22896097.7", Oct. 7, 2025, EPO, Germany.

Feng Qi et al., "Mechanistic studies for monodisperse exenatide-loaded PLGA microspheres prepared by different methods based on SPG membrane emulsification", Acta Biomaterialia, 2014, vol. 10, No. 10, pp. 4247-4256, England.

Joachim Herrmann et al., "Biodegradable, somatostatin acetate containing microspheres prepared by various aqueous and non-aqueous solvent evaporation methods " European Journal of Biopharmaceutics, 1998, vol. 45, No. 1, pp. 75-82, Netherlands.

Fuminori Ito et al., "Study of types and mixture ratio of organic solvent used to dissolve polymers for preparation of drug-containing PLGA microspheres" European Polymer Journal, 2009, vol. 45, No. 3, pp. 658-667, Netherlands.

Kyonghee Park et al., "Triptorelin acetate-loaded poly(lactide-co-glycolide) (PLGA) microspheres for controlled drug delivery" Macromolecular Research, 2012, vol. 20, pp. 847-851, Republic of Korea.

Phillip Van Der Peet, "Office Action for Australia Application No. 2022391391", Nov. 18, 2021, IP Australia, Australia.

Endrenyi, L. et al., "Cmax/AUC is a clearer measure than Cmax for absorption rates in investigations of bioequivalence", International Journal of Clinical Pharmacology, Therapy, and Toxicology. 1991, pp. 394-399, vol. 29, No. 10, University of Toronto, Canada.

Julia Koerner et al., "Harnessing Dendritic Cells for Poly(D,L-lactide-co-glycolide) Microspheres (PLGA MS)-Mediated Anti-tumor Therapy", Frontiers in Immunology, Apr. 5, 2019, vol. 10, Article 707.

Yichao Wang et al., "Manufacturing Techniques and Surface Engineering of Polymer Based Nanoparticles for Targeted Drug Delivery to Cancer", Nanomaterials, Feb. 1, 2016, vol. 6 No. 2, 26.

Cloutier, Adam, "Search Report for CA Application No. 3,236,685", Jan. 15, 2026, CIPO, Canada.

Abdul Ghani, Amylia, "Search Report for SG Application No. 11202402993S", Jan. 23, 2026, IPOS, Singapore.

Abdul Ghani, Amylia, "Written Opinion for SG Application No. 11202402993S", Jan. 24, 2026, IPOS, Singapore.

Tran, Susan T, "Office Action for U.S. Appl. No. 18/284,981", Feb. 11, 2026, USPTO, US.

Abdul Ghani, Amylia, "Written Opinion for SG Application No. 11202402988R", Jan. 24, 2026, IPOS, Singapore.

Examiner, "Office Action for EP Application No. 22896119.9", Jun. 12, 2026, EPO, Germany.

"Vivitrol PI": Vivitrol® package insert—Apr. 2006.

U.S. Food and Drug Administration, "Vivitrol® Product Specific Guidance," Draft Guidance on Naltrexone, Sep. 2015, U.S. Food and Drug Administration, USA.

Aulton, Michael E. et al., "Bioequivalence", extract from Alton's Pharmaceucs—The Design and Manufacture of Medicines, 2018, 356-360 pages, M. E. Aulton & K. M. G. Taylor, 5th edition, Elsevier.

Aulton, Michael E. et al., "Mean particle sizes", extract from Alton's Pharmaceutics—The Design and Manufacture of Medicines, 2018, 146-147 pages, M. E. Aulton & K. M. G. Taylor, 5th edition, Elsevier.

Verder Scientific, "Microtrac Product Overview": 'Microtrac Product Overview' from Microtrac website accessed Mar. 6, 2026 www.microtraccom/files/81269/productoverview. pdf.

Tran, Susan T, "Office Action for U.S. Appl. No. 18/284,981", Jul. 15, 2026, USPTO, US.

* cited by examiner

SUSTAINED-RELEASE INJECTABLE COMPOSITION CONTAINING NALTREXONE AND METHOD FOR PREPARING SAME

TECHNICAL FIELD

The present invention relates to a sustained-release injectable composition containing naltrexone and a method for producing the same.

BACKGROUND ART

Alcohol dependence refers to a condition in which there is always a compulsive desire to drink alcohol continuously or periodically to avoid the unpleasant feeling of lack of alcohol, and which causes various types of mental, physical and social disorders as a result of excessive and repeated intake of alcohol.

The Korea Institute for Health and Social Affairs reported that 26.1% of men, 10.5% of women, and 20.9% of all adults in Korea in 2001 were alcohol dependent. This means that 1 in 5 adults is alcohol dependent, and social problems and costs have increased due to alcohol dependence.

Naltrexone, an opioid receptor antagonist, has been used as a therapeutic for alcoholism since 1984 with approval from the U.S. Food and Drug Administration (FDA).

Naltrexone administered at a usual dosage (50 mg/person/day) is known to reduce the positive reinforcing effect of alcohol through increased opioid secretion by binding to and blocking opioid receptors, and long-term administration of naltrexone can increase the risk of liver cell damage.

It has been reported that, even when naltrexone is administered at a reduced dosage due to concerns about this side effect, it is effective in treating alcohol dependence.

However, even in the case of existing low-dose naltrexone tablets that are orally administered daily according to usual dosage regimens, there is a problem in that alcoholism patients worry about taking medicine and drinking alcohol every day, and thus cannot easily escape the temptation to consume alcohol.

To overcome this problem, naltrexone was developed as a long-acting injectable formulation whose effect lasts for one month after administered once. However, an excessive amount of the drug needs to be administered to maintain the effective plasma concentration of the drug, and thus a problem may arise in that initial burst release occurs, causing side effects.

In order to solve the above-described problems, there is a need to develop a sustained-release formulation containing naltrexone that may improve convenience of administration because of being injected once, and lower $C_{max}$ by controlling release, and at the same time, maintain the drug at the effective concentration or higher for one month.

PRIOR ART DOCUMENTS

Patent Documents (Patent Document 1) KR 10-2018-0129909 A1

DISCLOSURE

Technical Problem

An object of the present invention is to provide a sustained-release injectable composition containing naltrexone and a method for producing the same.

Another object of the present invention is to provide a sustained-release injectable composition containing naltrexone that may prevent initial burst release by controlling the release rate of naltrexone at a target site, and maintain a plasma naltrexone concentration sufficient to exhibit the effect of naltrexone by releasing naltrexone continuously for one month.

Still another object of the present invention is to provide a production method capable of producing microparticles that are homogeneous and of good quality while having high encapsulation efficiency for naltrexone, a poorly soluble drug.

Technical Solution

To achieve the above objects, the present invention provides a sustained-release injectable composition containing naltrexone, the composition comprising microparticles, wherein the microparticles may comprise naltrexone and a biodegradable polymer and have a value of 120 to 320 as calculated by the following Equation 1:

$$AUC_{inf}/C_{max} \quad \text{[Equation 1]}$$

wherein $AUC_{inf}$(ng*hr/ml) is the area under the plasma concentration-time curve, obtained by administering microparticles containing naltrexone to a beagle dog by injection and measuring the plasma concentration of naltrexone, and $C_{max}$ (ng/ml) is the maximum plasma concentration of naltrexone, measured after administering the microparticles containing naltrexone to the beagle dog by injection.

The microparticles may have a value of 0.8 to 1.5 as calculated by the following Equation 2:

$$\frac{D90 - D50}{D50 - D10} \quad \text{[Equation 2]}$$

wherein

D10 is the particle diameter corresponding to 10% in the cumulative size distribution of particles, D50 is the particle diameter corresponding to 50% in the cumulative size distribution of particles, and D90 is the particle diameter corresponding to 90% in the cumulative size distribution of particles.

The composition may contain more than 240 mg to less than 310 mg of naltrexone.

The biodegradable polymer may be selected from the group consisting of polylactic acid, polylactide, polylactic-co-glycolic acid, polylactide-co-glycolide (PLGA), polyphosphazine, polyiminocarbonate, polyphosphoester, polyanhydride, polyorthoester, polycaprolactone, polyhydroxyvalate, polyhydroxybutyrate, polyamino acid, and combinations thereof.

The microparticles may comprise naltrexone and the biodegradable polymer at a weight ratio of 1:1 to 1:10.

The sustained-release injectable composition, when administered by injection, may release naltrexone continuously for one month by controlling the release rate of naltrexone at a target site.

The injectable composition may contain a suspending solvent.

A method for producing a sustained-release injectable composition containing naltrexone according to another embodiment of the present invention comprises steps of: 1)

preparing an oil phase solution by dissolving naltrexone and a biodegradable polymer in a mixed solvent comprising at least two organic solvents; 2) preparing a water phase solution by dissolving a surfactant in water; 3) producing microparticles containing naltrexone using the oil phase solution and the water phase solution, and 4) mixing the microparticles with a suspending solvent, wherein the microparticles may have a value of 120 to 320 as calculated by the following Equation 1:

$$AUC_{inf}/C_{max} \quad \text{[Equation 1]}$$

wherein $AUC_{inf}$(ng*hr/ml) is the area under the plasma concentration-time curve, obtained by administering microparticles containing naltrexone to a beagle dog by injection and measuring the plasma concentration of naltrexone, and $C_{max}$ (ng/ml) is the maximum plasma concentration of naltrexone, measured after administering the microparticles containing naltrexone to the beagle dog by injection.

The mixed solvent comprises a first solvent and a co-solvent, wherein the first solvent may be dichloromethane.

The first solvent and the co-solvent may be comprised at a weight ratio of 1:0.5 to 1:10.

Advantageous Effects

According to the present invention, it is possible to prevent initial burst release by controlling the release rate of naltrexone at a target site and to maintain a plasma naltrexone concentration sufficient to exhibit the effect of naltrexone by releasing naltrexone continuously for one month.

In addition, the present invention provides a production method capable of producing microparticles that are homogeneous and of good quality while having high encapsulation efficiency for naltrexone, a poorly soluble drug.

Best Mode

The present invention provides a sustained-release injectable composition containing naltrexone, the composition comprising microparticles, wherein the microparticles may comprise naltrexone and a biodegradable polymer and have a value of 120 to 320 as calculated by the following Equation 1:

$$AUC_{inf}/C_{max} \quad \text{[Equation 1]}$$

wherein $AUC_{inf}$(ng*hr/ml) is the area under the plasma concentration-time curve, obtained by administering microparticles containing naltrexone to a beagle dog by injection and measuring the plasma concentration of naltrexone, and $C_{max}$ (ng/ml) is the maximum plasma concentration of naltrexone, measured after administering the microparticles containing naltrexone to the beagle dog by injection.

Mode for Invention

Hereinafter, embodiments of the present invention will be described in detail so that they can be easily carried out by those skilled in the art. However, the present invention may be embodied in various different forms and is not limited to the embodiments described below.

In the present invention, naltrexone may also be called N-cyclopropyl-methylnoroxymorphone, N-cyclopropylmethyl-14-hydroxydihydro-morphinone, 17-(cyclopropylmethyl)-4,5α-epoxy-3,14-dihydroxymorphinan-6-one, EN-1639A, or UM-792.

Naltrexone may be a compound represented by the following Formula:

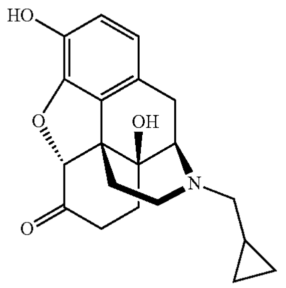

Naltrexone of the present invention may be in the form of a solvate, stereoisomer, prodrug, metabolite (e.g., 6β-naltrexol), derivative (e.g., naloxone), free base, or combination thereof, of naltrexone.

The stereoisomer refers to isomers that have the same molecular formula and sequence of bonded atoms, but differ in the arrangement of their atoms in space. The solvate refers to a compound solvated in an organic or inorganic solvent. The solvate is, for example, a hydrate. The stereoisomer may be a diastereomer or enantiomer. The prodrug may be a compound that changes into a target compound in vivo after administration of the compound. The metabolite may be a compound produced through an in vivo metabolic process. The derivative refers to a compound obtained by replacing part of the structure of naltrexone with another atom or atomic group.

A sustained-release injectable composition containing naltrexone according to one embodiment of the present invention comprises microparticles, wherein the microparticles may comprise naltrexone and a biodegradable polymer and have a value of 120 to 320 as calculated by the following Equation 1:

$$AUC_{inf}/C_{max} \quad \text{[Equation 1]}$$

wherein $AUC_{inf}$(ng*hr/ml) is the area under the plasma concentration-time curve, obtained by administering microparticles containing naltrexone to a beagle dog by injection and measuring the plasma concentration of naltrexone, and $C_{max}$ (ng/ml) is the maximum plasma concentration of naltrexone, measured after administering the microparticles containing naltrexone to the beagle dog by injection.

Naltrexone, a competitive antagonist with a high affinity for μ-receptors, has greater efficacy that can compete with other full agonists such as morphine or heroin.

Naltrexone, which has twice the antagonistic effect of naloxone, is used in opioid dependence treatment in several dosage forms, such as Revia (oral tablet) or Vivitrol (intramuscular injection).

The clinical dose ($C_{max}$) of Vivitrol is 380 mg, which is 3 to 4 times the daily oral dose of naltrexone (i.e., 50 mg) for 28 days.

In addition, various products of naltrexone hydrochloride are known, including combinations of naltrexone hydrochloride and other compounds. Examples thereof include Contrave (oral tablet; 8 mg naltrexone hydrochloride and 90 mg bupropion hydrochloride), Embeda (oral capsule; naltrexone hydrochloride and morphine sulfate at a ratio of 25:1), and Troxyca ER (oral capsule; 1.2 mg naltrexone hydrochloride and 10 mg oxycodone hydrochloride).

The above-described products are used to treat obesity or to relieve strong pain. Naltrexone, a non-selective opioid antagonist without agonist activity, may be used in combination with full opioid agonists (e.g., methadone) or opioid partial agonists (e.g. buprenorphine) to reduce opioid abuse during treatment.

As described above, the clinical dose ($C_{max}$) of Vivitrol, which is conventionally sold as a long-acting injection of naltrexone, is 380 mg, and Vivitrol is administered at an excessive dose to maintain the therapeutic effect of naltrexone continuously for one month. In other words, if Vivitrol is administered at a dose below the clinical dose, a problem arises in that it does not exhibit the therapeutic effect of naltrexone continuously for one month.

As described later, it can be seen that Vivitrol has a high $AUC_{inf}$ (area under the plasma concentration-time curve) value according to the administered dose, and shows initial burst release after administration.

Accordingly, when the value calculated by Equation 1 above for Vivitrol is checked, it can be seen that the value is below the lower limit of the range specified in the present invention. This result means that the majority of naltrexone is released in the initial stage after administration, even though the total amount of naltrexone released is large because the dose of naltrexone administered is high.

Specifically, in Equation 1 above, $AUC_{inf}$ refers to the degree of bioabsorption of naltrexone, and $C_{max}$ (ng/ml) refers to the maximum plasma concentration of naltrexone. Accordingly, the value calculated by Equation 1 above can indicate the relationship between the degree of bioabsorption of totally administered naltrexone and the maximum plasma concentration of naltrexone.

In order for the absolute value of Equation 1 to become larger, the value of $C_{max}$ should be smaller or the value of $AUC_{inf}$ should be larger. Therefore, an excessively small value of $C_{max}$ means that burst release of naltrexone does not occur. However, an excessively large value of $AUC_{inf}$ means that burst release of naltrexone occurs, which may cause problems associated with side effects of naltrexone.

On the other hand, in order for the absolute value of Equation 1 to become smaller, the value of $C_{max}$ should be larger or the value of $AUC_{inf}$ should be smaller. As described above, an excessively large value of $C_{max}$, which is larger than an appropriate maximum plasma concentration to exhibit the effect of naltrexone, means burst release of naltrexone, which may cause problems associated with side effects due to burst release, and an excessively small value of $AUC_{inf}$ means that the long-lasting effect of naltrexone for one month is not exhibited because the dose of naltrexone is low, or the bioabsorption rate of naltrexone is low.

Therefore, according to the present invention, the value calculated by Equation 1 above may be 120 to 320, 150 to 300, 170 to 280, 190 to 250, or 200 to 240. Within the above range, the dose of naltrexone contained in the sustained-release injectable composition may be at an appropriate level, and thus the composition may exhibit the effect of naltrexone continuously for one month and there is no burst release of naltrexone.

The dose of naltrexone in the composition may be greater than 240 mg to less than 310 mg, or 245 to 305 mg. When naltrexone is contained in the sustained-release injectable composition at a dose within the above range, naltrexone may exhibit its effect by being released continuously for one month.

The microparticles may have a value of 0.8 to 1.5 as calculated by the following Equation 2:

$$\frac{D90 - D50}{D50 - D10} \quad \text{[Equation 2]}$$

wherein

D10 is the particle diameter corresponding to 10% in the cumulative size distribution of particles, D50 is the particle diameter corresponding to 50% in the cumulative size distribution of particles, and D90 is the particle diameter corresponding to 90% in the cumulative size distribution of particles.

Here, D10, D50 and D90 refer to particle diameters corresponding to 10%, 50% and 90%, respectively, in the measured cumulative size distribution of the microparticles.

Equation 2 above defines the ratio of (D90-D50) to (D50-D10), which is the ratio of the difference between the particle diameter corresponding to 90% in the cumulative size distribution of the particles and the particle diameter corresponding to 50% to the difference between the particle diameter corresponding to 50% and the particle diameter corresponding to 10% in the cumulative size distribution of the particles. Equation 2 above represents particle size distribution uniformity, and a value closer to 1 as calculated by Equation 2 indicates a more uniform particle size distribution.

Equation 2 of the present invention is intended to more clearly define the size distribution of the microparticles, and the value calculated by Equation 2 may be 0.8 to 1.5, 0.8 to 1.2, 0.8 to 1.0, or 0.8 to 0.95. The average particle diameter (D50) of the microparticles, which satisfies the value calculated by Equation 2 above, may be greater than 30 μm to smaller than 90 μm, or 33 μm to 80 μm. The fact that the value calculated by Equation 2 above is included within the range specified in the present invention means that the size of the microparticles is distributed close to the average diameter value.

When the microparticles having a uniform size are administered in vivo by injection, they may be biodegraded at similar rates, and naltrexone may be effectively released by biodegradation of the microparticles.

In other words, for the microparticles containing naltrexone, the degree of release of naltrexone in vivo is highly correlated with the size and specific surface area of the microparticle, and in order to increase the specific surface area, it is essential to use microparticles with a uniform diameter. When the microparticles with a very uniform particle size as described above are used, they may prevent initial burst release of naltrexone after in vivo injection and exhibit the effect of releasing naltrexone continuously for a long period of time, thereby exhibiting the effect of naltrexone for one month.

In addition, if the average diameter (D50) of the microparticles is 90 μm or more, syringe clogging may occur during administration using a syringe. That is, if the microparticles have a large size, problems arise in that wettability is low and when the microparticles are mixed with a suspending solvent, they settle quickly even though they are temporarily dispersed quickly. Due to these problems, a problem arises in that layer separation between the microparticles and the suspending solvent occurs, and thus the microparticles do not pass through a needle 21 G during injection.

In order to overcome the above problems, it may be considered to use a different type of syringe (21 G or more). However, in this case, there is a problem that, since the needle is larger in diameter than a commonly used syringe, it may cause fear and pain.

The biodegradable polymer is selected from the group consisting of polylactic acid, polylactide, polylactic-co-glycolic acid, polylactide-co-glycolide (PLGA), polyphosphazine, polyiminocarbonate, polyphosphoester, polyanhydride, polyorthoester, polycaprolactone, polyhydroxyvalate, polyhydroxybutyrate, polyamino acid, and combinations thereof. Preferably, the biodegradable polymer is polylactide-co-glycolide (PLGA) or polylactide (PLA), without being limited to the above example.

In one example, the molar ratio of glycolide to lactide in polylactide-co-glycolide may be about 60:40 to about 90:10, about 60:40 to about 85:15, about 60:40 to about 80:20, about 60:40 to about 75:25, about 65:35 to about 90:10, about 70:30 to about 90:10, about 75:25 to about 90:10, about 65:35 to about 85:15, or about 70:30 to about 80:20, without being limited to the above examples. Preferably, the molar ratio of glycolide to lactide in polylactide-co-glycolide may be about 75:25.

The biodegradable polymer may comprise at least one polylactide and at least one polylactide-co-glycolide copolymer. In the present invention, the biodegradable polymer may comprise, for example, two polylactides, a combination of one polylactide and one polylactide-co-glycolide copolymer, two polylactide-co-glycolide copolymers, three polylactides, a combination of two polylactides and one polylactide-co-glycolide copolymer, a combination of one polylactide and two polylactide-co-glycolide copolymers, or the like. In particular, the biodegradable polymer may comprise a combination of one polylactide and one polylactide-co-glycolide copolymer, or two polylactide-co-glycolide copolymers, without being limited thereto.

The biodegradable polymer may comprise at least two polylactide-co-glycolide copolymers.

The microparticles may comprise naltrexone and the biodegradable polymer at a weight ratio of 1:1 to 1:10, 1:1 to 1:5, 1:1 to 1:4, or 1:2. Within the above range, the injectable composition may be prepared as a sustained-release injection that continuously releases naltrexone within the injectable dosage range for one month. In other words, if the weight ratio of naltrexone to the biodegradable polymer is below the lower limit of the above range, a problem may arise in that the amount of the injectable composition is increased to meet the total dose of naltrexone to be administered by injection, and the increased amount exceeds the amount of injection that may be administered once to a person. In addition, if the weight ratio of naltrexone to the biodegradable polymer is above the upper limit of the above range, a problem may arise in that it is not easy to produce microparticles in which naltrexone is uniformly distributed.

As described above, the sustained-release injectable composition containing naltrexone according to the present invention, when administered by injection, may release naltrexone continuously for one month by controlling the release rate of naltrexone at a target site. In addition, the composition may prevent initial burst release of naltrexone, unlike conventional sustained-release injectable formulations.

In general, side effects caused by naltrexone include complaints of feeling intoxicated or nausea. Additionally, these side effects usually appear within the first 30 days after administration of naltrexone.

This means that problems associated with side effects of naltrexone are serious when initial burst release of naltrexone after administration occurs.

In order to prevent these problems, in the present invention, microparticles having a uniform particle size and containing naltrexone evenly distributed therein are introduced into the sustained-release injectable composition by a production method described later, so that the composition may prevent initial burst release of naltrexone and release naltrexone continuously for one month.

In other words, according to the present invention, while naltrexone may be released at an effective plasma concentration equal to or higher than that can exert the effect of naltrexone, it is possible to prevent the initial burst release of naltrexone that can cause side effects, and to prevent naltrexone from being administered at an excessive dose in order to sustain the drug effect for one month.

The injectable composition may contain a suspending solvent, wherein the suspending solvent may comprise an isotonic agent, a suspending agent, and a solvent.

More specifically, the isotonic agent may be selected from the group consisting of D-mannitol, maltitol, sorbitol, lactitol, xylitol, sodium chloride, and mixtures thereof, and is preferably D-mannitol, without being limited to the above example.

The suspending agent may be selected from the group consisting of sodium carboxymethylcellulose, polysorbate 80, starch, starch derivatives, polyhydric alcohols, chitosan, chitosan derivatives, cellulose, cellulose derivatives, collagen, gelatin, hyaluronic acid (HA), alginic acid, algin, pectin, carrageenan, chondroitin, chondroitin sulfate, dextran, dextran sulfate, polylysine, titin, fibrin, agarose, fluran, xanthan gum, and mixtures thereof, and preferably comprises sodium carboxymethylcellulose and polysorbate 80, without being limited to the above example.

The solvent may be water for injection, and any solvent that may be used as water for injection may be used without limitation.

A method for producing a sustained-release injectable composition containing naltrexone according to another embodiment of the present invention comprises steps of: 1) preparing an oil phase solution by dissolving naltrexone and a biodegradable polymer in a mixed solvent comprising at least two organic solvents; 2) preparing a water phase solution by dissolving a surfactant in water; 3) producing microparticles containing naltrexone using the oil phase solution and the water phase solution, and 4) mixing the microparticles with a suspending agent.

The mixed solvent for dissolving naltrexone and the biodegradable polymer may comprise a first solvent and a co-solvent, wherein the first solvent may be dichloromethane.

In general, a solvent in which a drug and a biodegradable polymer are easily dissolved is generally used to produce microparticles using an organic solvent, wherein the solvent that is generally used may be dichloromethane.

However, even when the organic solvent such as dichloromethane is used, some poorly soluble drugs have low solubility. To solve this problem, the present invention is characterized in that a co-solvent is additionally used in addition to the first solvent to increase the solubility of naltrexone and to facilitate removal of the organic solvents later.

The co-solvent may have a density of 1.3 $g/cm^3$ or less, a polarity index of 3 or less, a boiling point of 50 °C or lower, or a water solubility of $2^{20}$ to $8^{20}$ g/100 g water. Specifically, the co-solvent may have a density of 1.3 $g/cm^3$ or less, 0.5 to 1.3 $g/cm^3$, 0.5 to 1.0 $g/cm^3$, or 0.6 to 0.9 $g/cm^3$.

In addition, the co-solvent may have a polarity index of 3 or less, 1 to 3, or 2 to 3.

In addition, the co-solvent may have a boiling point of 50 °C or lower, 30 °C to 50 °C, or 30 °C to 40 °C.

In addition, the co-solvent may have a water solubility of $2^{20}$ to $8^{20}$ g/100 g water, $3^{20}$ to $8^{20}$ g/100 g water, or $5^{20}$ to $8^{20}$ g/100 g water.

When a co-solvent that satisfies the above-described density, polarity index, boiling point or water solubility conditions is used in combination with the first solvent, it serves to help the first solvent and increase the solubility of naltrexone, a poorly soluble dry g. In addition, when the co-solvent is used in the process of removing residual organic solvents from the produced microparticles, the co-solvent may prevent the drug from being lost into the water phase solution while being removed earlier than the first solvent dichloromethane, and it may increase the concentration or viscosity of the biodegradable polymer present in the oil phase solution and increase the bonding strength between naltrexone and the biodegradable polymer, thus increasing the encapsulation efficiency of naltrexone in the biodegradable polymer.

In addition, since the co-solvent has a boiling point of 50 °C or lower, even when it is heated during the solvent removal process, it may not change the properties of the biodegradable polymer and may not change the release pattern of the microparticles. In addition, since the co-solvent has a low density, even when it is used in small amounts, it may lower the viscosity or density of the oil phase solution, thereby making it possible to produce microparticles that are uniform and of good quality.

The above-described co-solvent may specifically be a volatile organic solvent or a volatile non-polar organic solvent.

The volatile organic solvent may be selected from the group consisting of acetone, acetonitrile, benzene, butyl alcohol carbon disulfide, carbon tetrachloride, chloroform, cyclohexane, 1,1-dichloroethane, dimethoxyethane, ethanol, diethyl ether, ethyl acetate, heptane, hexane, methanol, methyl acetate, methyl t-butyl ether, pentane, propyl alcohol, tetrahydrofuran, and combinations thereof.

In addition, the volatile non-polar organic solvent may be selected from the group consisting of cyclohexane, pentane, hexane, heptane, carbon tetrachloride, carbon disulfide, benzene, diethyl ether, methyl t-butyl ether, tetrahydrofuran, ethyl acetate, and methyl acetate, chloroform, and combinations thereof.

When the co-solvent is used as a mixed solvent with the first solvent and acts together with the first solvent dichloromethane, it may lower the viscosity of the oil phase solution while increasing rather than decreasing the solubility of naltrexone or the biodegradable polymer, even though the co-solvent itself does not easily dissolve the naltrexone or the biodegradable polymer.

Also, as described above, the co-solvent may have the property of volatilizing or evaporating earlier than dichloromethane. In general, the transfer of naltrexone to a water phase solution occurs on the surfaces of microparticles that have not been completely dried, and as the internal viscosity increases and curing occurs while the organic solvent remaining in microparticles is removed, the reactivity with the water phase solution decreases, and thus the likelihood of naltrexone transfer into the water phase solution is lowered.

Accordingly, when a co-solvent having the above-described characteristics is used, the co-solvent may prevent naltrexone from being lost into the water phase solution while being removed earlier than the first solvent dichloromethane, and it may increase the concentration or viscosity of the biodegradable polymer present in the oil phase solution and increase the bonding strength between naltrexone and the biodegradable polymer, thus increasing the encapsulation efficiency of naltrexone in the biodegradable polymer.

In order to produce microparticles that are uniform and of good quality, the viscosity or density of the oil phase solution containing microparticles, the biodegradable polymer and the organic solvents is important. Since the co-solvent has a lower density than the first solvent, it may lower the density of the oil phase solution even when used in small amounts. Thus, when microparticles are to be produced by a microfluidic method, the co-solvent makes it possible to produce microparticles that are uniform and of good quality by allowing the oil phase solution and the water phase solution in the microchannel to be maintained in a laminar flow state and enables easy removal of residual organic solvents.

The co-solvent may preferably be diethyl ether or pentane, but is not limited to the above example, and it is possible to use, without limitation, any co-solvent that satisfies the above-described co-solvent conditions, increases the solubility of the poorly soluble drug naltrexone when used together with the first solvent, and has the property of volatilizing or evaporating earlier than the first solvent.

In step 1), the weight ratio between naltrexone and the mixed solvent may be about 1:7 to about 1:30, about 1:7 to about 1:29, about 1:7 to about 1:28, about 1:7 to about 1:27, about 1:7 to about 1:26, about 1:7 to about 1:25, about 1:7 to about 1:24, about 1:7 to about 1:23, about 1:7 to about 1:22, about 1:7 to about 1:21, about 1:7 to about 1:20, about 1:7 to about 1:19, about 1:7 to about 1:18, about 1:7 to about 1:17, about 1:7 to about 1:16, or about 1:7 to about 1:15, without being limited thereto.

In step 1), the weight ratio between naltrexone and the biodegradable polymer may be about 1:0.5 to about 1:10, about 1:0.5 to about 1:9, about 1:0.5 to about 1:8, about 1:0.5 to about 1:7, about 1:0.5 to about 1:6, or about 1:1 to about 1:5, without being limited thereto.

In step 1), the weight ratio between the co-solvent and the first solvent may be about 1:0.5 to about 1:10, about 1:0.5 to about 1:9, about 1:0.5 to about 1:8, about 1:0.5 to about 1:7, or about 1:0.5 to about 1:6, without being limited thereto.

Preferably, the weight ratio between naltrexone and the mixed solvent may be 1:15 to 1:20, and the weight ratio between the co-solvent and the first solvent may be 1:0.5 to 1:6, without being limited to the above examples. Naltrexone may be dissolved well within the above weight ratio range, and if the mixed solvent is used in an amount smaller than the lower limit of the above range, problems may arise in that naltrexone recrystallizes and precipitates, and the viscosity increases excessively, making filtration and production difficult. If the mixed solvent is used in excessively large amounts, there is no great problem in production, but the absolute amount of organic solvent used increases, and thus naltrexone may be lost into the water phase solution and it may be difficult to remove residual organic solvents.

The content of the biodegradable polymer in the mixed organic solvent may be, but is not limited to, about 5 to about 50 wt %, about 5 to about 40 wt %, about 5 to about 30 wt %, about 5 to about 20 wt %, about 5 to about 10 wt %, based on the amount of biodegradable polymer (e.g., polylactide-co-glycolide copolymer) used, without being limited thereto. The total amount of mixed organic solvent used may vary depending on the viscosity of the biodegradable polymer and the amount of naltrexone used. If the amount of naltrexone is large or the viscosity of the biodegradable polymer is high, the overall concentration may be lowered by increasing the amount of mixed organic solvent used. However, when the biodegradable polymer is dissolved in the mixed organic solvent within the above-described range, convenience in producing the microparticles may be achieved, and residual organic solvents may also be easily removed.

Contents regarding the biodegradable polymer are the same as described above, and thus detailed description thereof will be omitted.

The water phase solution may contain water and a surfactant. Here, as the surfactant, any surfactant that may help the oil phase solution form stable microparticles may be used without limitation.

Specifically, the surfactant may be at least one selected from the group consisting of nonionic surfactants, anionic surfactants, cationic surfactants, and combinations thereof. For example, the surfactant may be at least one selected from the group consisting of polyethylene glycol sorbitan monooleate, sorbitan oleate, sodium lauryl sulfate, polyvinyl alcohol (PVA), methylcellulose, polyvinylpyrrolidone, lecithin, gelatin, polyoxyethylene sorbitan fatty acid esters, polyoxyethylene castor oil derivatives, sodium stearate, ester amines, linear diamines, fatty amines, and combinations thereof, without being limited thereto.

The content of the surfactant in the water phase solution may be 0.1 to 1.0% (w/v), 0.2 to 0.8% (w/v), 0.25 to 0.7% (w/v), 0.4 to 0.6% (w/v), 0.4 to 0.5% (w/v), 0.5 to 0.6% (w/v), 0.1 to 0.3% (w/v), 0.2 to 0.3% (w/v), or 0.25 to 0.3% (w/v), without being limited thereto. For example, the water phase solution containing the surfactant may be a 0.5% (w/v) PVA solution, without being limited to the above example.

The viscosity of the oil phase solution in step 1) may be in a range in which the viscosity (unit: centipoise (cP)) of the fluid allows the fluid in the microchannel to be maintained in a laminar flow state. The viscosity of the fluid may be measured with a Brookfield Model LVT viscometer using an LV 01 or LV 02 spindle at 80 to 100 rpm. The viscosity of the oil phase solution is measured at 25 °C, and when the measurement is performed with a viscometer, a certain value of the viscosity is measured after the solution to be measured is stabilized. In general, it takes about 1 minute for the stabilization of the solution.

The oil phase solution of step 1) may have such a viscosity or density that it is maintained in a laminar flow state together with the water phase solution of step 2). Specifically, when the oil phase solution is introduced into the water phase solution flowing in the microchannel, the oil phase solution may have such a viscosity or density that the fluid in the microchannel is maintained in a laminar flow state. For example, the oil phase solution may have such a viscosity or density that the Reynolds number of the fluid flowing in the microchannel satisfies 2,300 or less.

The microparticles in step 3) may be produced using the oil phase solution and the water phase solution by an emulsion method, a porous membrane method, a spray-drying method, or a microfluidic method.

Specifically, the process of producing microparticles by the microfluidic method may comprise steps of: a) introducing the oil phase solution into a straight microchannel; b) introducing the water phase solution into a microchannel on one or either side; and c) collecting microparticles.

In step a), the oil phase solution is introduced into a straight microchannel and allowed to flow therethrough, and in step b), the water phase solution is introduced into a microchannel formed on one or either side so as to form an intersection point with the straight microchannel and allowed to flow therethrough. In other words, the oil phase solution may flow along the straight microchannel, and the water phase solution may flow along a microchannel, formed one or either side of the straight microchannel so as to form an intersection point with the straight microchannel, and meet the flow of the oil phase solution.

In addition, in order to make the water phase solution forming an intersection point with the flow of the oil phase solution flow at a higher flow rate than the oil phase solution introduced into the straight microchannel, the water phase solution is allowed to flow under higher pressure conditions.

By varying the flow rates of the oil phase solution and the water phase solution and making the flow rate of the water aqueous phase solution higher than the flow rate of the oil phase solution as described above, the water phase solution with a relatively higher flow rate may compress the oil phase solution at the point where the flow of the oil phase solution meets the flow of the water phase solution meet, and at this time, the biodegradable polymer and poorly soluble drug naltrexone in the oil phase solution may produce spherical microparticles due to the repulsive force between the oil phase solution and the water phase solution, and the spherical microparticles may have a structure in which the drug is evenly distributed in the spherical biodegradable polymer.

The method of producing microparticles by the microfluidic method is a method of forming microparticles of uniform size by introducing, into a microchannel, the oil phase solution in which naltrexone, the mixed organic solvent and the biodegradable polymer are dissolved, together with the water phase solution. This method may be a method of producing microparticles in the water phase solution. The micro-sized particles thus formed may be stabilized by the surfactant in the water phase solution, and as the organic solvents in the particles are evaporated or volatilized depending on the drying conditions, the organic solvent in the particles may be removed, thus forming microparticles.

The emulsion method may be a method comprising mixing the oil phase solution in which naltrexone, the mixed organic solvent and the biodegradable polymer are dissolved, and the water phase solution containing the surfactant, and then applying external energy (ultrasound, high-speed rotational force, etc.) to the mixture, causing the oil phase solution to form micro-sized particles in the water phase solution. As the organic solvent in the microparticles formed by the emulsion method is evaporated or volatilized depending on the drying conditions, the organic solvent in the particles may be removed, thus forming microparticles.

The porous membrane method is a method of producing microparticles by allowing the oil phase solution (dispersed phase), in which naltrexone, the mixed organic solvent and the biodegradable polymer are dissolved, to flow to one side of a porous membrane with micro-pores, and allowing the surfactant-containing water phase solution (continuous phase) to flow to the other side of the porous membrane to break the oil phase solution with the flow of the water phase solution.

The spray-drying method is a method of producing microparticles by spraying the oil phase solution, in which naltrexone, the mixed organic solvent and the biodegradable polymer are dissolved, in a spray dryer while blowing heated air, without using the water phase solution. In this method, micro-sized particles may be formed by atomizing the oil phase solution, and the organic solvent in the particles may be removed by evaporation or volatilization with heated air, thus forming microparticles.

Specific examples of the emulsion method and the spray-drying method are described, for example, in Koerner, J. (2019). Harnessing Dendritic Cells for Poly (D,L-lactide-co-glycolide) Microparticles (PLGA MS)—Mediated Anti-tumor Therapy. Frontiers, and Wang, Y (2016). Manufacturing Techniques and Surface Engineering of Polymer Based Nanoparticles for Targeted Drug Delivery to Cancer. Nanomaterials 6(2), 26, without being limited thereto.

Microparticles containing naltrexone according to another embodiment of the present invention are microparticles produced by the above-described production method.

The encapsulation efficiency for naltrexone in the microparticles may be about 90%, about 91%, about 92%, about 93%, about 94%, about 95%, about 96%, about 97%, about 98%, about 99%, or about 100%.

The microparticles may also be referred to as microspheres, and may refer to those particles which may contain naltrexone as an active ingredient therein.

Experimental Example 2

Experiment for Comparing Encapsulation Efficiency for Naltrexone Microparticles, Residual Organic Solvent, and Dissolution According to Solvent (1) Production of Microparticles Containing Naltrexone Microparticles for use in the experiment were produced as follows, and the contents of the components used in the production of the microparticles are summarized in Table 1 below.

Example 1

0.5 g of naltrexone in free base form and 1.0 g of a DL-lactide/glycolide copolymer were mixed and dissolved in 10.0 g of dichloromethane and 2.3 g of diethyl ether. The resulting oil phase solution was applied to each microchannel to produce microparticles at the intersection between the oil phase solution and the water phase solution, and the microparticles were collected in the water phase solution) (10 °C). The water phase solution was a 0.5% (w/v) PVA solution (0.5% (v/v) PVA in water).

The produced microparticles were stirred at 10 °C for 1 hour, at 30 °C for 1 hour, and then at 50 °C for 1 hour to remove the organic solvents. The produced microparticles were sieved and then freeze-dried, thereby producing dried microparticles.

Example 2

Microparticles were produced in the same manner as in Example 1, except that 8.0 g of dichloromethane and 2.0 g of diethyl ether were used.

Comparative Example 1

Microparticles were produced in the same manner as in Example 1, except that no diethyl ether was used and 8.0 g of dichloromethane was used.

Comparative Example 2

Microparticles were produced in the same manner as in Example 1, except that no diethyl ether was used and 12.3 g of dichloromethane was used.

TABLE 1

| | Comparative Example 1 | Comparative Example 2 | Example 1 | Example 2 |
|---|---|---|---|---|
| Naltrexone | 0.5 g | 0.5 g | 0.5 g | 0.5 g |
| 75/25 DL-lactide/glycolide copolymer | 1.0 g | 1.0 g | 1.0 g | 1.0 g |
| Dichloromethane | 8.0 g | 12.3 g | 10.0 g | 8.0 g |
| Diethyl ether | — | — | 2.3 g | 2.0 g |

(2) Comparison of Encapsulation Efficiency, Residual Organic Solvent, and Precipitation According to Use of Co-Solvent and Amount of Organic Solvent For the microparticles produced in Experimental Example 1(1), solubility, encapsulation efficiency, and residual organic solvent were assessed. Whether naltrexone and the biodegradable polymer were dissolved was checked visually based on whether precipitation occurred, and the encapsulation efficiency was measured using high-performance liquid chromatography (HPLC). Residual organic solvents were analyzed through gas chromatogram (GC). The results are shown in Table 2 below.

TABLE 2

| | Encapsulation efficiency (%) | Residual organic solvent (ppm) | Remarks |
|---|---|---|---|
| Comparative Example 1 | — | — | Precipitated |
| Comparative Example 2 | 84.67 | Dichloromethane: 1,764.2 | — |
| Example 1 | 90.97 | Dichloromethane: 806.9; diethyl ether: 322.9 | — |
| Example 2 | 93.08 | Dichloromethane: 1,000.5; diethyl ether: 289.8 | — |

As a result of comparing Comparative Example 1 and Comparative Example 2, it was confirmed that, if the amount of dichloromethane was insufficient, naltrexone dissolved in the organic solvent was precipitated due to recrystallization during the process of preparing the oil phase solution (because naltrexone is poorly soluble in dichloromethane), and thus microparticles could not be produced. As a result of comparing Comparative Example 2 with Examples 1 and 2, it was confirmed that, when diethyl ether was used as a co-solvent, the encapsulation efficiency increased by about 6% compared to when dichloromethane was used alone, and in this case, the amount of the residual organic solvent dichloromethane was reduced, and the total amount of residual organic solvents was also reduced.

From the above results, it can be seen that the effect of increasing the encapsulation efficiency was obtained by using dichloromethane in combination with diethyl ether, which has a boiling point lower than that of dichloromethane. This is believed to be because the solvent diethyl ether volatilized at a lower temperature than dichloromethane, and thus the concentrations of naltrexone and the biodegradable polymer in the microparticles increased, increasing the viscosity of the oil phase solution present in the microparticles, thereby increasing the bonding strength between naltrexone and the biodegradable polymer.

Experimental Example 2

Experiment for Comparing Encapsulation Efficiency for Naltrexone Microparticles, Residual Organic Solvent, and Dissolution According to Mixing Ratio of Solvents (1) Production of Microparticles Containing Naltrexone Microparticles for use in the experiment were produced as follows, and the contents of the components used in the production of the microparticles are summarized in Table 4 below.

Example 3

0.5 g of naltrexone and 1.0 g of a DL-lactide/glycolide copolymer were mixed and dissolved in 6.0 g of dichloromethane and 2.0 g of diethyl ether. The resulting oil phase solution was applied to each microchannel to produce microparticles at the intersection between the oil phase solution and the water phase solution, and the microparticles were collected in the water phase solution)(10 °C). The water phase solution was a 0.5% (w/v) PVA solution. The produced microparticles were stirred at 10 °C for 1 hour, at 30 °C for 1 hour, and then at 50 °C for 1 hour to remove the organic solvents. The produced microparticles were sieved and then freeze-dried, thereby producing dried microparticles.

Example 4

Microparticles were produced in the same manner as in Example 3, except that microparticles were stirred at 10 °C for 1.5 hours, at 30 °C for 1.5 hours, and then at 50 °C for 1.5 hours to remove the organic solvents.

Example 5

Microparticles were produced in the same manner as in Example 3, except that 3.0 g of diethyl ether was used.

TABLE 3

| | Example 3 | Example 4 | Example 5 |
|---|---|---|---|
| Naltrexone | 0.5 g | 0.5 g | 0.5 g |
| 75/25 DL-lactide/glycolide copolymer | 1.0 g | 1.0 g | 1.0 g |
| Dichloromethane | 6.0 g | 6.0 g | 6.0 g |
| Diethyl ether | 2.0 g | 2.0 g | 3.0 g |

(2) Comparison of Encapsulation Efficiency for Naltrexone Microparticles, Residual Organic Solvent, and Dissolution According to Mixing Ratio of Solvents

TABLE 4

| | Encapsulation efficiency (%) | Residual organic solvent (ppm) | Remark |
|---|---|---|---|
| Example 3 | 98.97 | Dichloromethane: 1,360.0; diethyl ether: 264.2 | — |
| Example 4 | 90.70 | Dichloromethane: 1,827.7; diethyl ether: 427.3 | — |

TABLE 4-continued

| | Encapsulation efficiency (%) | Residual organic solvent (ppm) | Remark |
|---|---|---|---|
| Example 5 | 101.19 | Dichloromethane: 1,207.2; diethyl ether: 344.9 | — |

As a result of comparing Example 3 and Example 4, it could be confirmed that, as the stirring time to remove the organic solvents increased, the encapsulation efficiency decreased rather than increased. In addition, it was confirmed that an increase in the stirring time to remove the organic solvents led to no significant change in the amount of residual organic solvent.

As a result of comparing Example 3 and Example 5, it was confirmed that the ratio between dichloromethane and diethyl ether used as the organic solvents affected the encapsulation efficiency. It can be seen that, as the ratio of diethyl ether to dichloromethane increased, the encapsulation efficiency for naltrexone in the microparticles increased.

Experimental Example 3

Particle Size Analysis

To specifically examine the diameter of the microparticles, analysis was performed using a Microtrac particle size analyzer.

For the microparticles produced in the same manner as in Example 1, particle size analysis was performed three times.

D10 to D90 are given in units of μm, and the experimental results are shown in Table 5 below.

TABLE 5

| | OP-185-40 | OP-185-41 | OP-185-42 | Vivitrol |
|---|---|---|---|---|
| D10 | 33.61 | 34.24 | 33.35 | 46.40 |
| D20 | 35.28 | 36.00 | 34.94 | 56.61 |
| D30 | 36.62 | 37.31 | 36.26 | 63.94 |
| D40 | 37.73 | 38.30 | 37.43 | 70.52 |
| D50 | 38.74 | 39.24 | 38.46 | 77.05 |
| D60 | 39.71 | 40.14 | 39.48 | 84.01 |
| D70 | 40.73 | 41.11 | 40.51 | 92.24 |
| D80 | 41.82 | 42.11 | 41.67 | 103.2 |
| D90 | 43.22 | 43.46 | 43.09 | 122.2 |
| Width | 7.66 | 7.23 | 7.78 | 55.98 |
| Mean (MV) | 38.61 | 39.09 | 38.37 | 82.41 |
| SD | 3.83 | 3.61 | 3.89 | 27.99 |
| $\frac{D90 - D50}{D50 - D10}$ | 0.87 | 0.84 | 0.91 | 1.47 |

It was confirmed that the microparticles produced in Example 1 had D50s of 38.74 μm, 39.24 μm, and 38.46 μm, respectively, and had standard deviations of 3.83, 3.61, and 3.89, indicating that they had very uniform particle sizes.

As a result of performing the same particle size analysis (PSA) for Vivitrol, it was confirmed that the D50 thereof was 77.05 μm and the standard deviation thereof was 27.99, indicating that Vivitrol included particles of various diameters.

In addition, it was confirmed that the values calculated by the equation (D90-D50)/(D50-D10) as shown in Table 5 above were uniform without a significant differences between Examples 1 to 3. On the other hand, it was confirmed that the value calculated by the equation for Vivitrol was 1.47, which was significantly different from the value for the microparticles of the present invention.

Experimental Example 4

Pharmacokinetic Analysis

Pharmacokinetic evaluation of the sustained-release injectable composition of the present invention was performed.

Compositions for subcutaneous injection were prepared by adding 2.0 mL (per vial) of a suspending solvent to the microparticles of Example 1 and then uniformly suspending them.

The suspending solvent had the composition shown in Table 6 below.

TABLE 6

| Total content | Purpose of addition | Component | Amount | Unit |
|---|---|---|---|---|
| Per 2.0 mL | Isotonic agent | D-Mannitol | 100.0 | mg |
| | Suspending agent | Sodium carboxy-methylcellulose | 10.0 | mg |
| | Suspending agent | Polysorbate 80 | 20.0 | mg |
| | Solvent | Water for injection | Remainder | |

The compositions for injection were prepared by adding the microparticles so that the compositions contained 200 mg, 245 mg and 300 mg of naltrexone, respectively.

Each of the compositions for injection was administered to a beagle dog by subcutaneous (SC) injection, and the plasma naltrexone concentration was measured over time. As a control, Vivitrol, which is currently on sale, was purchased and administered to a beagle dog, and the plasma naltrexone concentration was measured in the same manner. The analysis results are shown in Table 7 below.

TABLE 7

| Time | Vivitrol | 200 | 245 | 300 |
|---|---|---|---|---|
| 0 | 0 | 0.00 | 0.00 | 0 |
| 0.5 | 15.675 | 3.85 | 4.61 | 5 |
| 1 | 19.505 | 6.20 | 8.07 | 8.37 |
| 2 | 15.51 | 5.92 | 6.62 | 6.995 |
| 4 | 11.46 | 4.68 | 5.20 | 5.385 |
| 6 | 7.53 | 4.53 | 6.61 | 5.25 |
| 8 | 5.58 | 4.82 | 8.41 | 4.545 |
| 12 | 3.675 | 5.74 | 9.30 | 5.25 |
| 18 | 4.515 | 7.89 | 17.09 | 6.865 |
| 24 | 6.515 | 13.83 | 14.36 | 18.32 |
| 48 | 128.475 | 17.99 | 44.29 | 57.585 |
| 72 | 75.25 | 11.35 | 14.45 | 28.755 |
| 120 | 22.65 | 11.27 | 13.81 | 16.015 |
| 168 | 45.535 | 19.97 | 15.53 | 20.95 |
| 240 | 20.785 | 12.73 | 18.84 | 17.365 |
| 336 | 17.705 | 14.27 | 19.86 | 27.41 |
| 504 | 6.165 | 4.40 | 10.66 | 8.675 |
| 576 | 5.305 | 1.31 | 4.52 | 8.445 |
| 672 | 2.98 | 0.30 | 2.07 | 3.975 |
| 744 | 2.085 | 0.14 | 1.77 | 2.825 |
| 840 | 0.73 | 0.03 | 0.48 | 1.23 |
| AUC(last) | 14874.9 | 6540.75 | 9817.98 | 11831.76 |
| AUC(inf) | 15038.37 | 6542.81 | 9874.26 | 12060.41 |
| Cmax (ng/ml) | 128.475 | 19.97 | 44.29 | 57.585 |
| Tmax | 48 | 168.00 | 48.00 | 48 |
| AUC(inf)/Cmax | 117.05 | 327.63 | 222.95 | 209.44 |

From the above experimental results, it was confirmed that the maximum plasma concentration ($C_{max}$) of naltrexone for Vivitrol was at 48 hours after administration. In addition, it can be seen that there was a difference in the AUC measurement results, considering the dose of naltrexone contained in Vivitrol.

On the other hand, it could be seen that, although the microparticle composition of the present invention, which contained 245 mg of naltrexone, had a lower dose of naltrexone than Vivitrol, it released naltrexone continuously for one month, and showed a plasma naltrexone concentration similar to that of Vivitrol even at 672 hours.

In addition, it can be confirmed that, even when the composition of the present invention, which contained 300 mg of naltrexone, was administered, it exhibited the effect of naltrexone for one month. It can be confirmed that, when the composition of the present invention, which contained 300 mg of naltrexone, was administered, it showed the $C_{max}$ at 48 hours, like Vivitrol, but the value of the $C_{max}$ was less than half of the $C_{max}$ value of Vivitrol, indicating that the composition of the present invention is effective in suppressing the initial burst release of naltrexone, even if the administration dose of naltrexone increases.

In conclusion, the sustained-release injectable composition containing naltrexone according to the present invention is capable of maintaining the effect of naltrexone continuously for one month after administration while suppressing the initial burst release of naltrexone compared to Vivitrol.

Although the preferred embodiments of the present invention have been described in detail above, the scope of the present invention is not limited thereto, and various modifications and improvements can be made by those skilled in the art without departing from the basic concept of the present invention as defined in the following claims and also fall within the scope of rights of the present invention.

Industrial Applicability

The present invention relates to a sustained-release injectable composition containing naltrexone and a method for producing the same.

The present invention was supported by the following national research and development project.

[Project Serial Number] 1465031634

[Grant Number] HI20C0936

[Government Department] The Ministry of Health and Welfare

[Project Management Agency] Korea Health Industry Development Institute

[Research Project Name] R&D linked to biohealth investment infrastructure

[Research Task Name] Development of long-acting injectable formulation for treatment of opioid and alcohol dependence using controlled and optimized production technology

[Contribution Rate] 1/1

[Agency Carrying Out Project] Inventage Lab Inc.

[Research Period] Jan. 1, 2022 to Dec. 31, 2022

The invention claimed is:

1. A sustained-release injectable composition, the composition comprising:

microparticles comprising naltrexone and a biodegradable polymer, the microparticles having a value of 120 to 320 according to a following Equation 1:

$$AUC_{inf}/C_{max} \quad \text{[Equation 1]}$$

wherein the $AUC_{inf}$ (ng*hr/ml) denotes an area under a plasma concentration-time curve, obtained by administering the microparticles to a beagle dog by injection and measuring a plasma concentration of the naltrexone, and wherein the $C_{max}$ (ng/ml) denotes a maximum plasma concentration of the naltrexone, measured after administering the microparticles to the beagle dog by injection, wherein the microparticles have a value of 0.8 to 1.2 according to a following Equation 2:

$$\frac{D90 - D50}{D50 - D10} \quad \text{[Equation 2]}$$

wherein D10 denotes a particle diameter corresponding to 10% in a cumulative size distribution of the microparticles, wherein D50 denotes a particle diameter corresponding to 50% in the cumulative size distribution of the microparticles, and wherein D90 denotes a particle diameter corresponding to 90% in the cumulative size distribution of the microparticles.

2. The sustained-release injectable composition according to claim 1, containing more than 240 mg to less than 310 mg of naltrexone.

3. The sustained-release injectable composition according to claim 1, wherein the biodegradable polymer is selected from the group consisting of polylactic acid, polylactide, polylactic-co-glycolic acid, polylactide-co-glycolide (PLGA), polyphosphazine, polyiminocarbonate, polyphosphoester, polyanhydride, polyorthoester, polycaprolactone, polyhydroxyvalate, polyhydroxybutyrate, polyamino acid, and combinations thereof.

4. The sustained-release injectable composition according to claim 1, wherein the microparticles comprise naltrexone and the biodegradable polymer at a weight ratio of naltrexone to the biodegradable polymer of 1:1 to 1:10.

5. The sustained-release injectable composition according to claim 1, wherein, when administered by injection, the sustained-release injectable composition releases naltrexone continuously for one month by controlling a release rate of naltrexone at a target site.

6. The sustained-release injectable composition according to claim 1, further containing a suspending solvent.

7. A method for producing a sustained-release injectable composition according to claim 1 containing naltrexone, the method comprising steps of:

1) preparing an oil phase solution by dissolving naltrexone and a biodegradable polymer in a mixed solvent comprising at least two organic solvents;
2) preparing a water phase solution by dissolving a surfactant in water;
3) producing microparticles containing naltrexone using the oil phase solution and the water phase solution, and
4) mixing the microparticles with a suspending solvent.

8. The method according to claim 7, wherein the mixed solvent comprises a first solvent and a co-solvent, wherein the first solvent is dichloromethane.

9. The method according to claim 8, wherein the first solvent and the co-solvent are comprised at a weight ratio of the first solvent to the co-solvent of 1:0.5 to 1:10.

* * * * *